United States Patent [19]

Edwards et al.

[11] Patent Number: 5,195,996
[45] Date of Patent: Mar. 23, 1993

[54] OSTOMY DEVICE WITH IMPROVED COUPLING SYSTEM

[75] Inventors: John V. Edwards, Reigate, England; Walter F. Leise, Jr., Yardley, Pa.; John B. Cline, New Brunswick, N.J.

[73] Assignee: E. R. Squibb & Sons, Princeton, N.J.

[21] Appl. No.: 639,105

[22] Filed: Jan. 9, 1991

Related U.S. Application Data

[62] Division of Ser. No. 530,635, May 30, 1990, Pat. No. 5,088,992.

[51] Int. Cl.$^5$ .............................................. A61F 5/44
[52] U.S. Cl. .................................... 604/338; 604/332; 604/342
[58] Field of Search ............................... 604/327-332, 604/335-339, 342

[56] References Cited

U.S. PATENT DOCUMENTS

4,170,231 10/1979 Collins ............................... 604/344
4,872,869 10/1989 Johns ................................. 604/342
4,892,530 1/1990 Steer ................................. 604/338

FOREIGN PATENT DOCUMENTS

2148716 6/1985 United Kingdom ................ 604/339

Primary Examiner—Randy C. Shay
Assistant Examiner—Gina M. Gualtieri
Attorney, Agent, or Firm—James & Franklin

[57] ABSTRACT

In the first embodiment, the faceplate coupling ring is of conventional design and includes an axially extending rib with a radially outwardly extending rim and a radially inwardly extending deflectable sealing strip. The pouch coupling ring includes inner and outer spaced walls, forming a channel for receiving the rib. First and second protrusions extend inwardly from points on the interior surface of the walls proximate the ends thereof. The first protrusion cooperates with the rim and the second protrusion cooperates with the tip of the sealing strip, to securely retain the rib within the channel. The walls of the channel have reduced thickness and are easily deflectable as the rib is inserted into the channel, such that coupling of the rings is facilitated but decoupling requires the conventional amount of force due to the second protrusion. In the second embodiment, the deflectable sealing strip on the faceplate coupling ring is replaced by a rigid flange which cooperates with the second protrusion to substantially increase the decoupling force.

8 Claims, 6 Drawing Sheets

OSTOMY DEVICE WITH IMPROVED COUPLING SYSTEM

This is a divisional of U.S. Ser. No. 530,635 filed on May 30, 1990, now U.S. Pat. No. 5,088,992.

The present invention relates to ostomy devices of the type including releasable inter-engaging parts in the form of coupling rings adapted to permit detachment of the collection pouch from the adhesive backed faceplate and, more particularly, to a pouch coupling ring structure which substantially reduces the required coupling force to facilitate mounting of the pouch and a faceplate coupling ring structure which substantially increases the required uncoupling force to enhance security.

Subsequent to ileostomy, colostomy and similar surgical procedures, it is often necessary for a patient to utilize an ostomy pouch to cover the stoma and collect waste material as it is discharged. Over the years, ostomy pouches of a variety of different sizes, shapes and constructions have been utilized. Various materials and medical grade adhesives have been developed to increase the utility and the wearability of the pouches.

The basic collection article includes first and second thin film plastic walls which are sealed, by heat welding or the like, along the periphery to form the contour of a bag or pouch. An adhesive backed faceplate is designed to secure the pouch to the skin surrounding the stoma. The faceplate and pouch have openings adapted to align with the stoma.

Recent improvements have extended the period during which the faceplate can be worn to be longer than normally required for a pouch to be filled to capacity with waste material. Moreover, with respect to new users in particular, it may be necessary to frequently remove the device to provide access to the skin surrounding the stoma and the stoma itself. Removal of the faceplate permits observation and checking of the condition of the skin surrounding the stoma and if necessary, treatment of same. Thus, inspite of the improvements in faceplate materials and adhesives, frequent removal of the device, due to cleaning of the pouch and checking for treatment of the skin surrounding the stoma, and the stoma, can be required.

However, frequent removal of the faceplate from the skin is to be avoided. The skin surrounding the stoma is often extremely sensitive and may comprise a healing incision or scar tissue. Frequent removal of an adhesive backed faceplate can lead to skin stripping and irritation. One popular solution to this problem is to provide an ostomy device wherein the pouch is removably mounted to the faceplate. In this so called "two piece" device, the faceplate can remain affixed to the skin for an extended period to time, but the pouch may be removed for observation and treatment of the stoma and replaced as necessary.

The two piece device requires a means for releasably mounting the pouch to the faceplate. One particularly successful structure takes the form of a pair of annular or ring-like rigid or semi-rigid plastic parts, one in the form of an axially extending rib and the other in the form of a channel into which the rib may be removably received and frictionally engaged.

When the faceplate is mounted to the skin, the pieces of the ostomy device are assembled by applying a force on the exterior portion of the pouch, over the inter-engaging coupling rings, in a direction towards the body, along the axis of the rings. This force must be of significant magnitude to result in coupling and is absorbed by the skin beneath the faceplate. However, since the skin under the faceplate may be sensitive, particularly immediately following the surgical procedure creating the stoma, applying sufficient force to the skin to cause engagement of the coupling rings can be painful.

One extremely commercially successful coupling ring structure is disclosed in U.S. Pat. No. 4,460,363 to Steer et al, issued Jul. 1984. That patent discloses a pair of coupling rings, one of which includes an axially extending rib which carries a radially outwardly extending rim and an inwardly extending sealing strip, which is extremely resilient. The other coupling ring includes a channel formed by relatively rigid spaced walls. One of the walls has an radially inwardly extending protrusion which cooperates with the radially outwardly extending rim on the rib to retain the rib within the channel. The the sealing strip is deflected or deformed by channel walls, as the rib is received. The deflected sealing strip applies a force on the rib in the direction of the rim to maintain the rib securely within the channel.

This structure works well, particularly for patients on which the peristomal skin has healed, such that the force of coupling can be absorbed. However, for patients who have relatively recently experienced surgery, and hence have an extremely sensitive peristomal area, this configuration may cause discomfort or even damage, because it requires a relatively large coupling force to mount the pouch.

Unfortunately, it is not possible to simply reduce the amount of the force necessary to cause frictional engagement between the coupling rings. This would also result in a reduction of the force necessary to detach the pouch from the label, thereby increasing the possibility of accidental detachment, a result which is to be avoided.

One way to avoid this problem is to modify the manner in which the coupling ring is mounted to the faceplate. Instead of being welded directly to the faceplate surface, the coupling ring mounting has been made flexible to permit the user to temporarily lodge his finger between the surface of the faceplate and the coupling ring, as the pouch is attached. In this manner, the axially directed force applied to couple the rings is absorbed by the fingers instead of the sensitive skin surrounding the stoma. One successful embodiment of this flexible mounting is disclosed in U.S. Pat. No. 4,846,820 issued Jul. 11, 1989 to Ole R. Jensen and entitled "Ostomy Device".

The Jensen device described in U.S. Pat. No. 4,846,820 utilizes an expandable part, preferably including one or more accordion like folds, which is interposed between the faceplate surface and the coupling ring. The expandable section permits the fingers of the user to be positioned between the ring and the faceplate so as to absorb the attachment force.

The Jensen structure permits the attachment of the coupling ring without the application of force on the peristomal surface, However, it has a relatively complicated structure requiring additional manufacturing operations and hence increased cost.

It is, therefore, a prime object of the present invention to provide an ostomy device with an improved coupling system wherein, in a first preferred embodiment, the coupling force is greatly reduced as compared to the conventional configurations.

It is another object of the present invention to provide an ostomy device with an improved coupling system where, in a second preferred embodiment, the coupling force is reduced and, in addition, the uncoupling force is increased so as to result in a more secure engagement.

It is another object of the present invention to provide an ostomy device with an improved coupling system which includes a reinforced pull tab to assist in overcoming the increase uncoupling force.

It is another object of the present invention to provide an ostomy device with an improved coupling system which, in the first preferred embodiment, includes an improved channel structure with oppositely radially extending protrusions from the interior walls thereof, so as to engage the rim and sealing strip, respectively, extending from the rib.

It is another object of the present invention to provide an ostomy device with an improved coupling system wherein, in the second preferred embodiment, the rib of the coupling ring is provided with a non-deflectable sealing flange.

It is another object of the present invention to provide an ostomy device with an improved coupling system in which the walls of the channel have reduced thickness and hence enhanced flexibility so as to facilitate insertion of the rib into the channel.

SUMMARY OF THE INVENTION

In accordance with one aspect of the present invention, an ostomy device is provided comprising waste collection means, faceplate means attachable to a peristomal surface and means for detachably mounting the collection means on the faceplate. The mounting means includes first and second coupling means affixed to the collection means and faceplate means, respectively. One of the coupling means includes substantially axially extending rib means, substantially radially outwardly extending rim means and substantially inwardly extending sealing strip means. The other of the coupling means includes channel means for removably receiving the rib means. The channel means includes inner and outer spaced walls, each having an interior surface. The channel includes first and second protrusions extending from points on the interior surfaces proximate the ends of the walls. The first protrusion cooperates with the rim means and the second protrusion cooperates with the strip means to securely retain the rib means within the channel means.

The outer channel wall is preferably comprised of relatively thin, deflectable material. The strip means cooperates with the second protrusion to temporarily deflect the outer wall as the rib means is inserted within the channel means, to facilitate coupling of the coupling means.

The strip means is composed of relatively resilient material such that it is deformed relative to its original position when the rib means is situated within the channel means as to retain the rib means securely within the channel means.

A second preferred embodiment is composed of substantially non-deformable material. It comprises a flange with a generally solid triangular cross-sectional configuration.

The flange is defined by a first surface extending substantially radially inwardly from the interior surface of the rib means and a second surface extending at an incline from a point approximate the edge of the first surface to a point on the interior surface of the rib means proximate the edge thereof.

In the second preferred embodiment, the outer wall is retained in its deflected condition to a significant degree by the flange when the rib means is situated within the channel means. This increases the force necessary to uncouple the coupling means.

The device further comprises reinforced pull tab means extending substantially radially outwardly from the channel means. The pull tab means preferably comprises spaced rib means which act to reinforce same.

In accordance with another aspect of the present invention, an ostomy device is provided comprising waste collection means, faceplate means attachable to a peristomal surface and means for detachably mounting the collection means on the faceplate means. The mounting means comprises first and second coupling means affixed to the collection means and the faceplate means, respectively. One of the coupling means comprises substantially axially extending rib means, substantially radially outwardly extending rim means and substantially inwardly extending substantially non-deformable sealing flange means. The other coupling means includes channel means for removably receiving the rib means. The channel means comprises inner and outer spaced walls, each having an interior surface. The inner wall and the outer wall comprise first and second protrusions extending from points on the interior surfaces proximate the ends of the walls. The outer wall is formed of substantially deflectable material. The non-deformable sealing flange means causes the inner wall to deflect to a significant degree when the rib means is received within the channel means. The first protrusion cooperates with the rim means. The second protrusion on the deflectable inner wall cooperates with the non-deflectable flange means to securely retain the rib means within the channel means.

The flange means has a generally solid triangular cross-sectional configuration. The flange means is defined by a first surface substantially radially inwardly extending from the interior surface of the rib means and a second surface extending at an incline from a point proximate the edge of the first surface to a point on the interior surface of rib means proximate the edge thereof.

A reinforced pull tab means extending substantially radially outwardly from the channel means is provided. The pull tap means comprises spaced rib means.

In accordance with another object of the present invention, an ostomy device is provided including waste collection means, faceplate means attachable to a peristomal surface and means for detachably coupling the collection means and the faceplate means. The coupling means includes first and second coupling rings affixed to the collection means and the faceplate means, respectively. The first coupling means includes substantially radially extending pull tab means. The pull tab means comprises a base, and means for reinforcing the base to increase the strength thereof.

The reinforcing means preferably comprises spaced, substantially parallel reinforcing rib means. The rib means not only increase the structural strength of the tab, but also facilitate the gripping thereof.

BRIEF DESCRIPTION OF THE DRAWINGS

To these and such other objects which may hereinafter appear, the present invention relates to an ostomy device with an improved coupling system as described in the following specification and recited in the annexed claims, taken together with the accompanying drawings, wherein like numerals refer to like parts and in which:

FIG. 3 is a front elevational, partially cut-away, view of an ostomy device of the present invention;

As shown in FIGS. 3 and 5, the ostomy device of the present invention includes a substantially planar flexible faceplate, generally designated A, which includes a layer of medical grade adhesive forming the body side surface 11 and a thin film of polymeric material forming the pouch side 13 of the faceplate. The adhesive permits the faceplate to be affixed to the peristomal skin surface in a conventional manner. Faceplate A is provided with a central opening 10, designed to align with the stoma and to be enlarged in accordance with the size of the stoma.

A collection receptacle, generally designated B, in the form of a pouch or bag, is provided for attachment to faceplate A. Pouch B is formed of two thin transparent or translucent sheets of flexible plastic material which are heat welded around the periphery 12, so as to form a waste collection receptical. Pouch B, is provided with an opening 14 which is defined by a first coupling ring, generally designated C. Opening 14 is positioned on pouch B so as to aligned with stoma receiving opening 10 when the pouch is mounted on the faceplate. Stoma receiving opening 10 is within an area on faceplate A which is defined by a second coupling ring, generally designated D, which is affixed thereto. Coupling rings C and D may be affixed to the pouch B and faceplate A respectively by welding, adhesives or other conventional affixation means appropriate for plastic elements.

Figure 1:
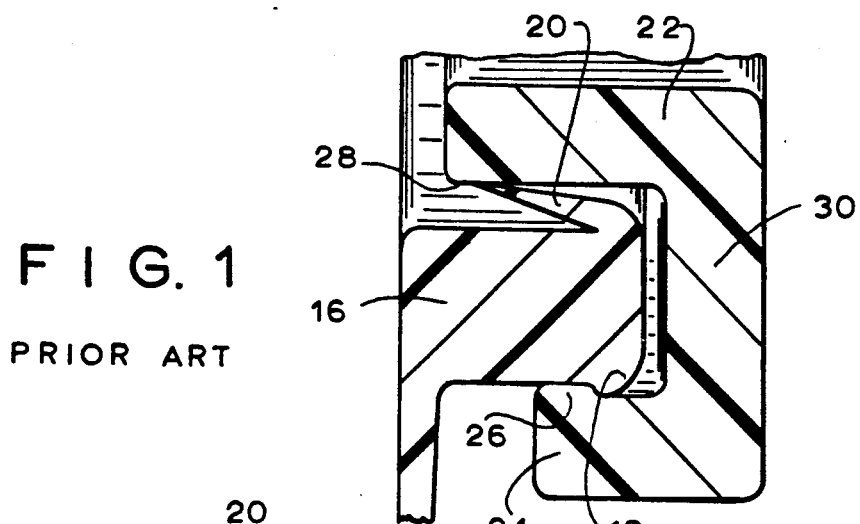
FIG. 1 is an enlarged cross-sectional view of assembled coupling rings of prior art configuration.
Figure 2:
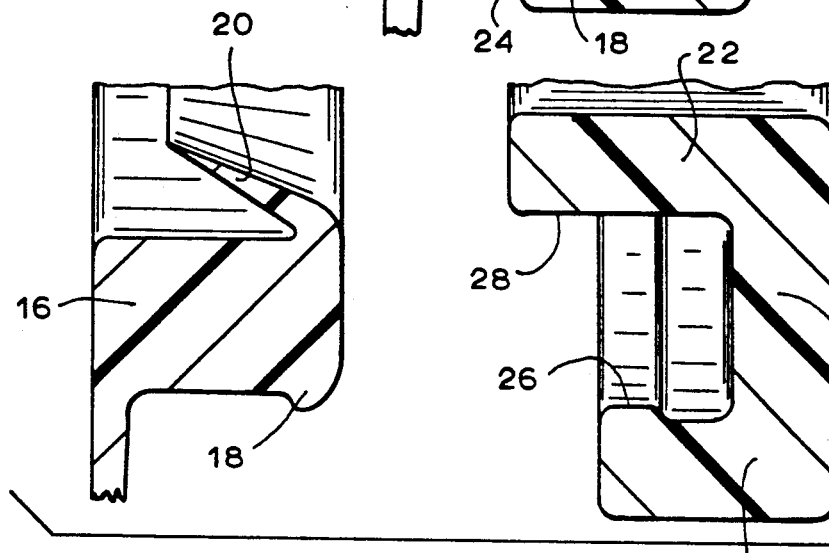
FIG. 2 is a view similar to FIG. 1, but showing the coupling rings in exploded position.

FIGS. 1 and 2 are enlarged cross-sectional views of a prior art coupling ring structure which is commercially available from the ConvaTec of Princeton, N.J. and which is disclosed in the above mentioned Steer, U.S. Pat. No. 4,460,363. As shown in those figures, the male coupling ring, designed to be affixed to the faceplate, includes a generally axially extending rib 16 which has an exterior surface with a radially outwardly (in a direction away from the stoma) extending rim 18, proximate the forward edge thereof. The interior surface is provided with a relatively highly deflectable sealing strip 20, which has a generally tapered cross-sectional configuration and which extends inwardly (in a direction toward the stoma) from the forward edge of the interior surface of rib 16 towards the faceplate surface at an acute angle with respect to the rib surface.

The female coupling ring includes an interior wall 22, and a shorter exterior wall 24, which are spaced apart by a wall 30 to form a channel adapted to receive rib 16 therein. The interior surface of exterior wall 24 is provided with a radially inwardly directed protrusion 26. The interior surface 28 of exterior wall 22 is planar, being devoid of any protrusion.

As rib 16 is inserted into the channel defined by wall 22 and 24, sealing strip 20 is deflected in a counter-clockwise direction (as seen in FIGS. 1 and 2). Protrusion 18 on rib 16 passes over protrusion 26 on wall 24 and lodges in the recess between protrusion 26 and the interior surface of wall 30. As seen in FIG. 1, when rib 16 is fully inserted in the channel, sealing strip 20 is substantially deflected from its normal position and cooperates with the interior surface 28 of interior wall 22 so as to exert a force on rib 16 in a direction towards exterior wall 24 to maintain protrusion 18 in the recess formed by protrusion 26 and hence maintain a relatively secure coupling between the coupling rings.

It should be noted, however, that in this configuration, there is no protrusion on the interior surface 28 of the interior wall 22, to cooperate with the tip of sealing strip 20. In addition, the channel walls 22, 24 are relatively thick. Hence, the walls are relatively rigid. They are not deflected or deformed by the insertion of rib 16 to any substantial degree. It is only sealing strip 20 which is deflected by insertion.

Figure 6:
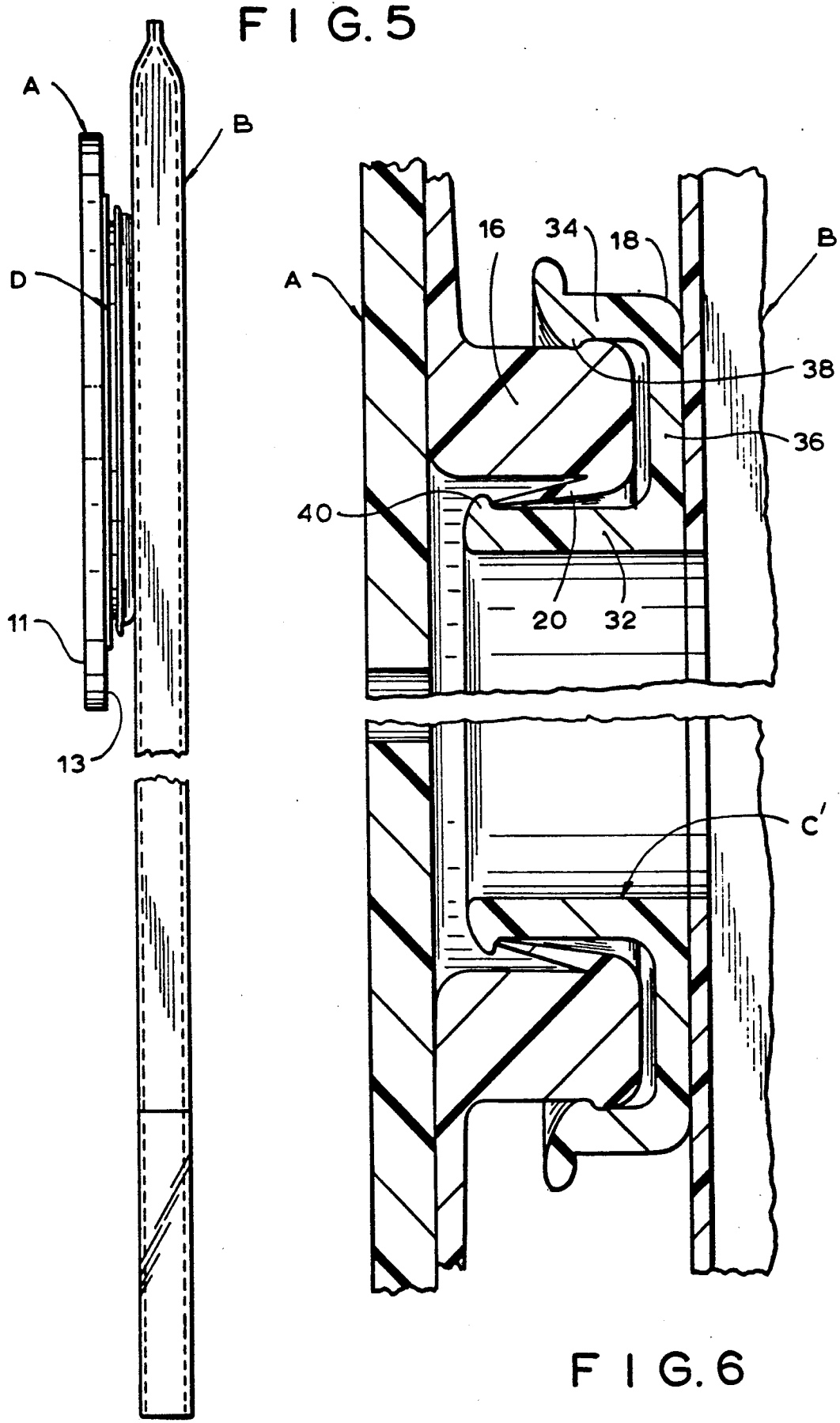
FIG. 6 is an enlarged cross-sectional view taken along line 6—6 of FIG. 3.
Figure 7:
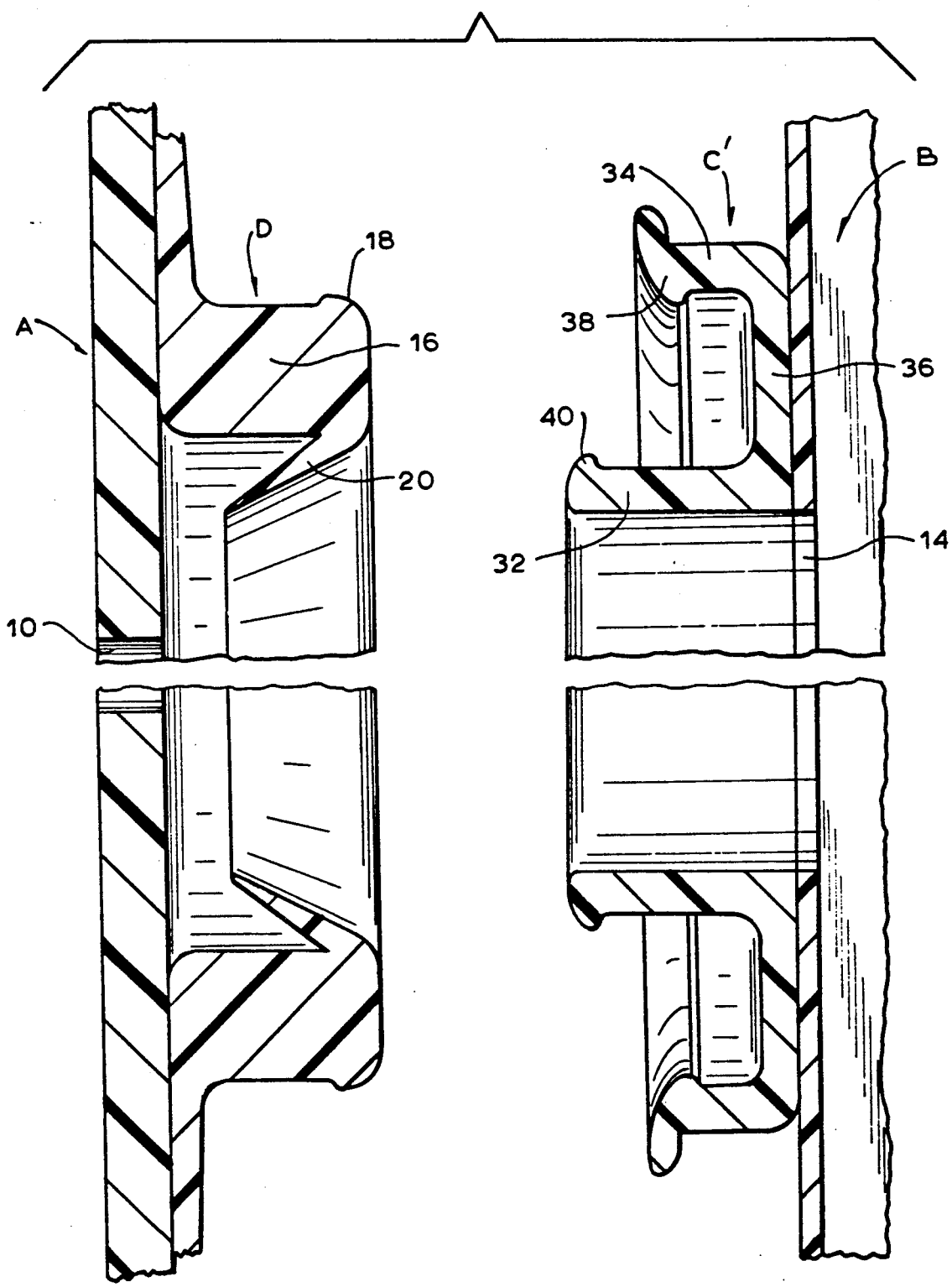
FIG. 7 is a view similar to FIG. 6 but showing the coupling rings in exploded position.

FIGS. 6 and 7 depict the first preferred embodiment of the present invention. In this embodiment, the coupling ring D affixed to faceplate A is identical to the corresponding part in the prior art. Only the coupling ring (now designated as C'), designed to be affixed to the pouch B, has an improved structure. This improvement results in a reduction in the amount of force necessary to couple the coupling rings without materially affecting the amount of force which is necessary to detach the rings, as compared to the prior art. Accordingly, the first preferred embodiment of the present invention is extremely useful in situations where substantial pressure on the area surrounding the stoma is contra-indicated, such as immediately after surgery or where the skin surrounding the stoma has yet to heal or is irritated for some reason, but normal uncoupling force must be maintained.

Coupling ring C' include a channel similar in configuration to the channel of coupling ring C with two major differences. The first difference is the addition of an radially inwardly (toward the interior of the channel) directed protrusion adapted to cooperate with deflectable sealing strip 20. The second modification has to do with the flexibility of the walls of the channel which, because they have substantially reduced thickness as compared to the prior art, are substantially more deflectable, thereby greatly facilitating the insertion of the rib into the channel. The protrusion cooperates with the tip of the sealing strip to maintain a relatively high uncoupling force while the reduced wall thickness facilitates coupling, thereby reducing the coupling force.

Coupling ring C' comprises an interior wall 32 and exterior wall 34 connected by wall 36 which define the rib receiving channel. The interior surface of exterior wall 34 is provided with an radially inwardly directed protrusion 38 which has the same function as protrusion 26 on coupling ring C, that is, to cooperate with rim 18 on the rib to secure the rib within the channel. The exterior wall 34 tends to be cammed outwardly as the rib is inserted, mainly because of the cooperation between protrusion 38 and rim 18 and the relative flexibility of exterior wall 34 due to the reduced thickness thereof.

Figure 5:
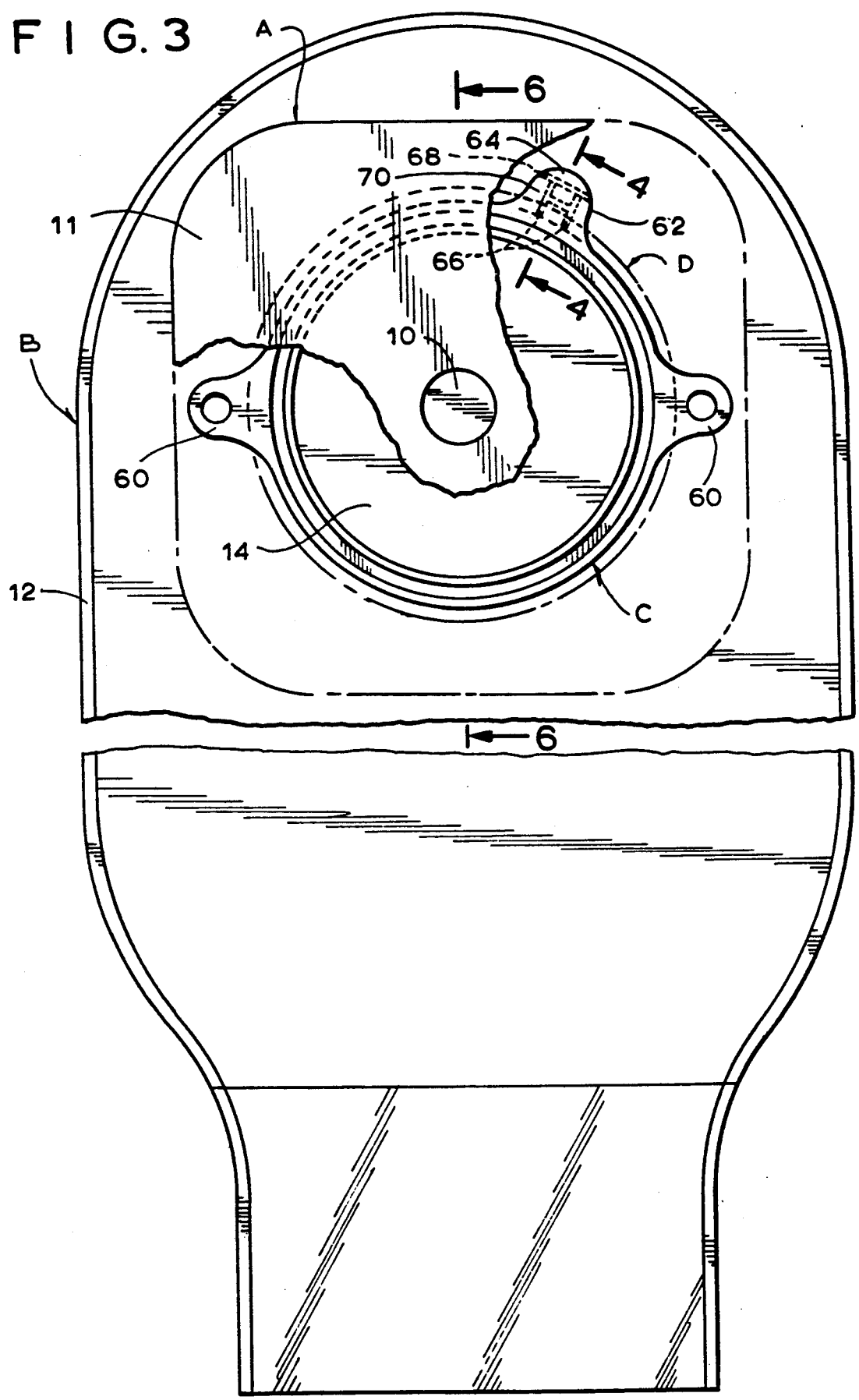
FIG. 5 is a side elevational view of the ostomy device shown in FIG. 3.

The interior surface of interior wall 32 is provided with a radially inwardly extending protrusion 40, which is adapted to cooperate with sealing strip 20, so as to facilitate the deflection of the sealing strip as the rib is received within the channel and thereafter to create a recess for nesting the sealing strip 20 between protrusion 40 and the interior surface of wall 36, as is illustrated in FIG. 5. Protrusion 40 cooperates with the tip of sealing strip 20 to maintain the rib in the channel. It should be appreciated that interior wall 32 will tend to deflect towards the center of coupling ring C' as rib 16 is received within the channel, such that in this embodiment, two deflections occur at the same time, the deflection of sealing strip 20 toward rib 16 and the deflection of interior wall 32 away from rib 16, so as to facilitate insertion of the rib within the channel. The reduction in coupling force is mainly due to the flexibility of interior wall 32 which, unlike in the prior art, is no longer rigid or semi-rigid because of the reduced thickness thereof.

It has been determined experimentally that when coupling ring C' of the first preferred embodiment of the invention is utilized, the force necessary to obtain coupling is approximately one half of the force required coupling the prior art structure. Accordingly, an approximately 50% reduction in application force is achieved with the first preferred embodiment of the present invention.

Figure 9:
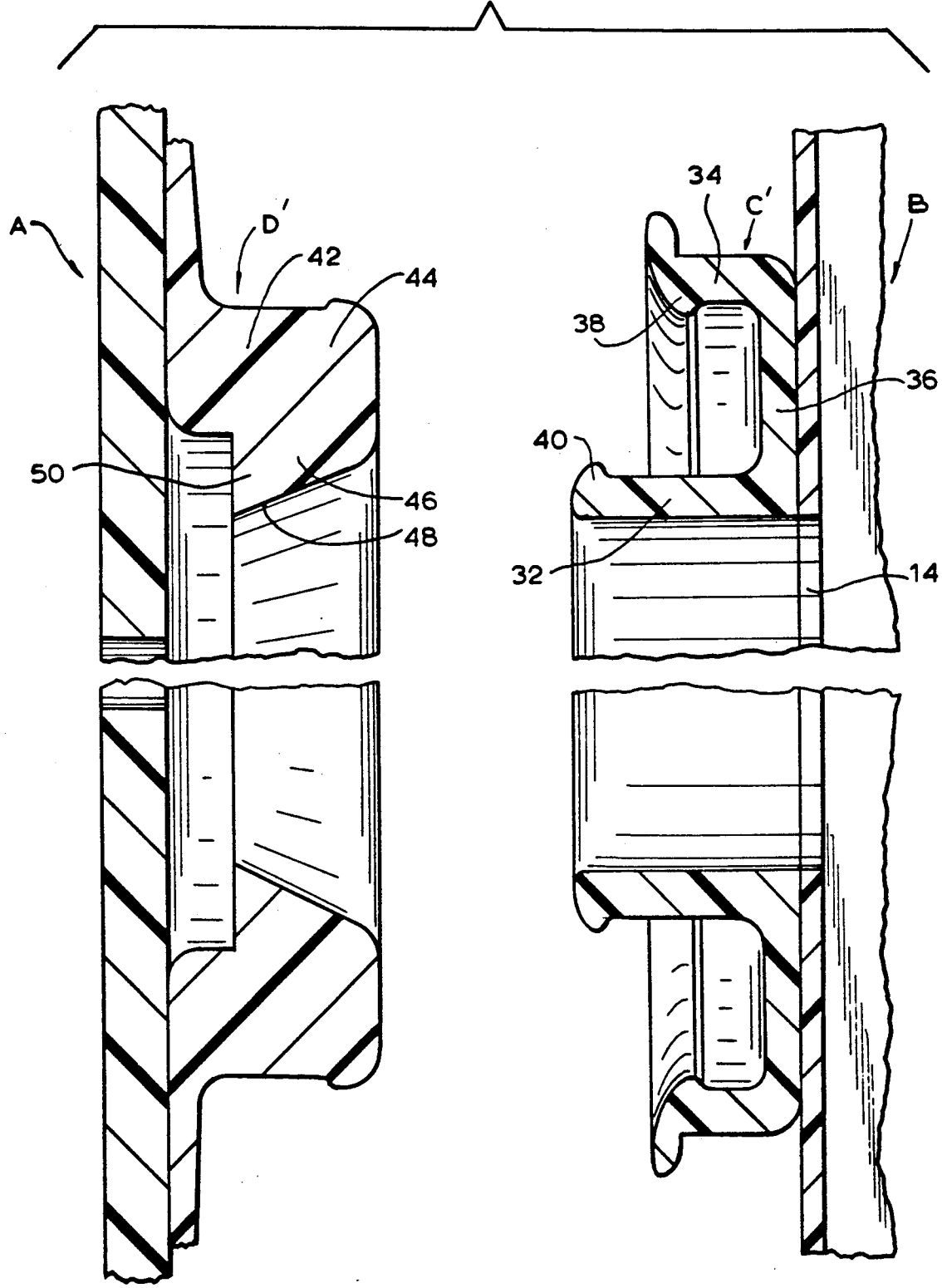
FIG. 9 is a view similar to FIG. 8 but showing the coupling rings of the second preferred embodiment in exploded position.
Figure 8:
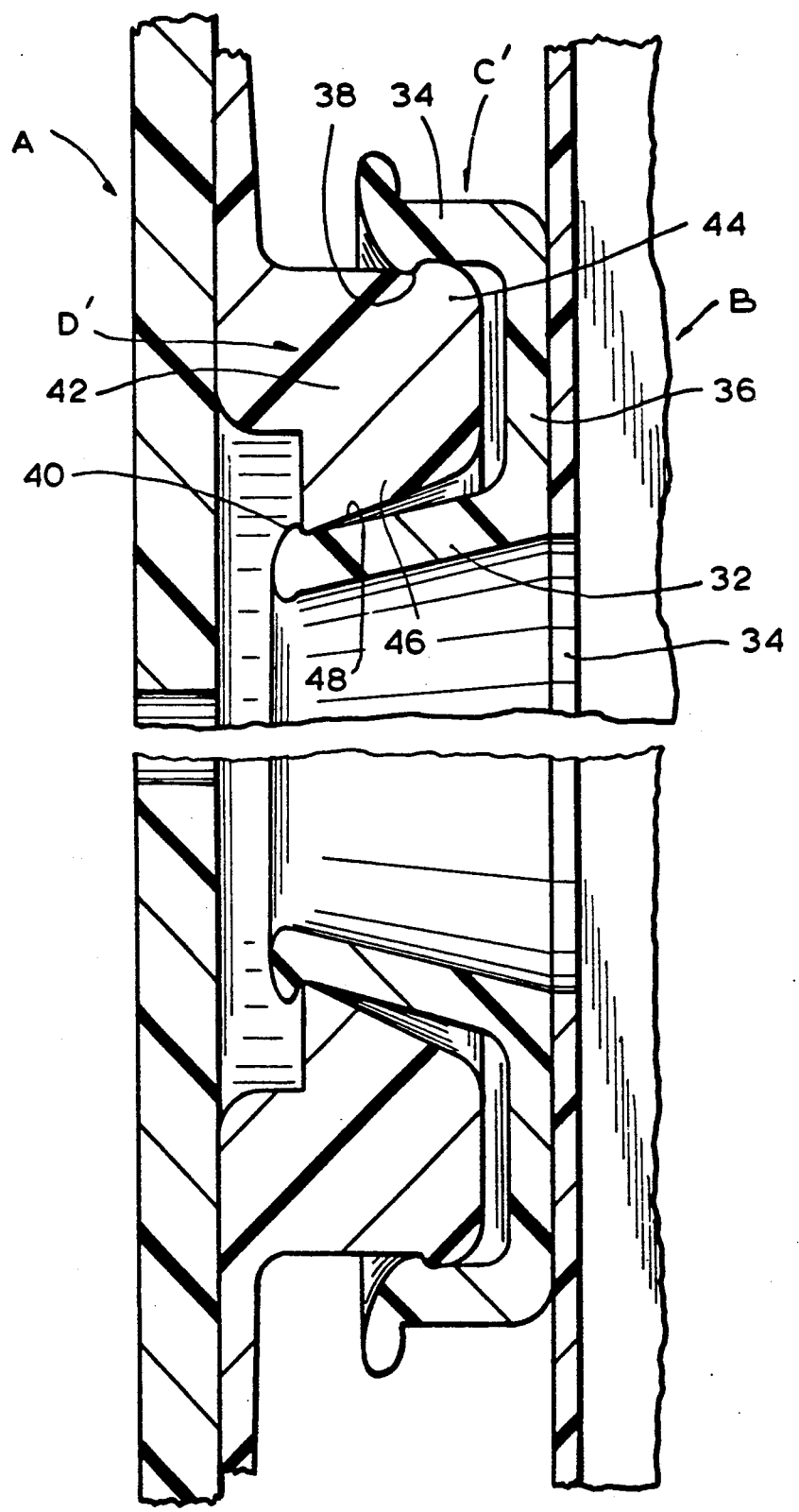
FIG. 8 is an enlarged side cross-sectional view of a second preferred embodiment of the coupling rings of the present invention.

The second preferred embodiment of the present invention is depicted on FIGS. 8 and 9. In the second preferred embodiment, the channel of coupling ring C' is identical to that described with respect to the first preferred embodiment. However, in this case, the structure of the rib of the faceplate coupling ring (now denoted as D') is also improved. This improvement substantially increases the amount of force necessary to uncouple the rings.

Coupling ring D' includes an axially extending rib 42 with a radially extending rim 44 similar to the corresponding parts of coupling ring D. However, in coupling ring D', the deflectable sealing strip 20 has been replaced with a solid, substantially rigid sealing flange 46. Flange 46 has an exterior surface 48 which substantially coincides in position with the exterior surface of strip 20, when strip 20 is in the non-deflected position. However, instead of forming the sealing strip as a tapered body, the interior recess thereof is now filled with solid plastic such that the flange is not deflectable or deformable to any appreciable degree.

When rib 42 is inserted within the channel of coupling ring C', as is shown in FIG. 8, interior channel wall 32 is deflected towards the center of the coupling ring as it is in the first embodiment when rib 16 is received within the channel. However in, this embodiment, because sealing flange 46 is non-deflectable, the wall 32 will remain in a deflected condition as long as rib 42 is within the channel. Rim 44 will cooperate with inwardly directed protrusion 38 to maintain the rib within the channel, as in the previous embodiment. In addition, in this embodiment, the tip of sealing flange 46 will cooperate with an inwardly extending protrusion 40 on interior wall 32, so as to provide an additional means of maintaining the rib within the channel. Accordingly, significantly more force is required to uncouple the coupling rings of the second preferred embodiment, as compared to the first preferred embodiment or the prior art. Hence, the second preferred embodiment is much easier to couple but much more difficult to uncouple as compared to the prior art.

The second preferred embodiment of the present invention depicted in FIGS. 8 and 9 has another advantage over the prior art and first embodiment of the present invention. As shown in FIGS. 1 and 6, a space is present between rib 16 and the deflectable sealing strip 20. Fecal matter can become trapped within this space presenting the user with an unsightly condition which is difficult to clean. The solid sealing flange 46, on the other hand, does not have a space in which fecal matter can be trapped and its surface is easily cleaned if soiled.

It has been determined experimentally that the uncoupling force required for the second preferred embodiment can be as much as five times the force necessary to uncouple the coupling rings of the first preferred embodiment. Hence, the second preferred embodiment is significantly more secure and reduces the possibility of accidental detachment to a great extent as compared to both the first preferred embodiment and the prior art.

Referring again to FIG. 3, it is common with respect to pouch coupling rings to provide outwardly extending tabs 60 to permit the pouch coupling ring to be attached to a body encircling belt or strip for added security. Such tabs are normally integrally molded with the coupling ring when the ring is formed. Similarly, it is common to provide the pouch coupling ring with a grip or pull tab 62 so as to give the user a convenient way to grasp the coupling ring as it is pulled away from the faceplate to detach the coupling rings.

Figure 4:
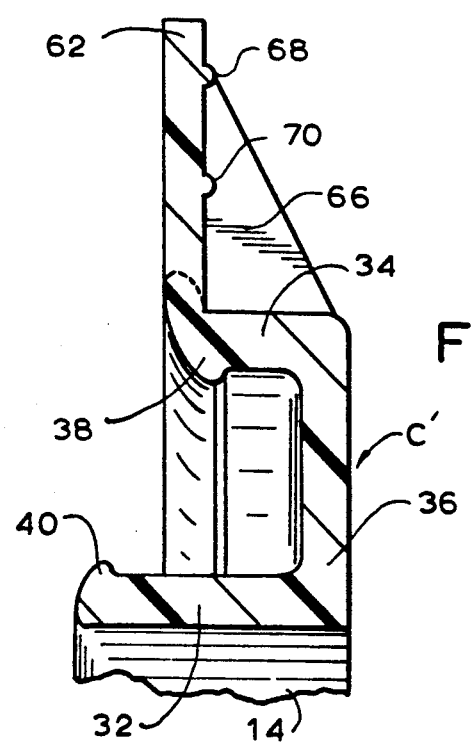
FIG. 4 is a cross-sectional view taken along line 4—4 of FIG. 3.

However, it has been found that with the second preferred embodiment of the present invention, in particular, because of the substantially increased uncoupling force necessary to detach the pouch from the faceplate, pull tabs of conventional construction often bend before the rings are uncoupled. Accordingly, as best seen in FIG. 4, a reinforced pull tab 62 is provided. Pull tab 62 comprises a base 64 and a pair of reinforcing ribs 66 spaced from each other across base 64 and extending along base 64 away from wall 32. In particular, reinforcing ribs 66 have a substantially triangular configuration and extend from the base 64 to the outside of exterior wall 34 which is substantially perpendicular thereto, creating a right triangle. This reinforces the structure of the pull tab 62 by rigidifying the base 64 and preventing same from moving an appreciable distance out of the plane which is substantially perpendicular to wall 34.

In addition, base 64 may be provided with a pair of spaced transversely extending ribs 68, 70 which facilitate the gripping of the pull tab by providing a more textured surface. The use of reinforcing ribs 66 results in a pull tab 62 which is sufficiently rigid that it cannot be bent or damaged when used with coupling rings of increased coupling force.

It should now be appreciated that the present invention is an ostomy device in which the force necessary to couple the coupling rings is substantially reduced. This reduction in coupling force is a result of reduced thickness channel walls which are substantially more easily deflected by the rib as it is inserted and the use of an additional protrusion which cooperates with the tip of deflected sealing strip to offset the effect of the more deflectable channel walls, so as to maintain the uncoupling force substantially equal to that of the prior art while permitting the coupling force to be substantially reduced. In a second preferred embodiment, the deflectable sealing strip is replaced by a non-deflectable sealing flange which is used on a rib in conjunction with the modified channel to maintain the substantially reduced coupling force of the first preferred embodiment but substantially increased the uncoupling force, as compared to the first preferred embodiment and the prior art. The result, therefore, in a second preferred embodiment, is a coupling system which has reduced coupling force but increased security. In addition, a reinforced pull tab is provided for use with the second preferred embodiment of the present invention to overcome the increased uncoupling force.

While only a limited number of preferred embodiments have been disclosed for purposes of illustration, it is obvious that many variations and modifications could be made thereto. For example, the orientation of the deflectable sealing strip or non deflectable flange on the one hand and the rim on the other hand could be reversed in the coupling rib, provided of course that the structure of the channel is correspondingly altered. In addition, the rib could be affixed to the pouch and the channel to the faceplate, if desired. It is intended to cover all of these variations and modifications, which fall within the scope of the present invention, as defined by the following claims:

We claim:

1. An ostomy device comprising waste collection means, faceplate means attachable to a peristomal surface and means for detachably mounting said collection means on said faceplate means, said mounting means comprising first and second coupling means affixed to said collection means and said faceplate means, respectively, one of said coupling means comprising substantially axially extending rib means comprising a body rim means extending in a substantially radial direction from and outwardly of said body, and sealing flange means extending in said substantially radial direction from and inwardly from said body, said body being substantially non-deformable in said radial direction, said other of said coupling means comprising channel means for removably receiving said rib means, said channel means comprising spaced inner and outer walls and a connecting wall, each having an interior surface, said outer wall and said inner wall comprising first and second protrusions, respectively, extending from points on said interior surfaces of said outer and inner walls proximate the ends of said walls remote from said connecting wall, said inner wall being formed of substantially deflectable material, said flange means causing said inner wall to deflect to a significant degree when said rib means is received in said channel means, said first protrusion cooperating with said rim means and said second protrusion cooperating with said flange means to securely retain said rib means within said channel means.

2. The device of claim 1 wherein said sealing flange means has a generally solid triangular cross-sectional configuration.

3. The device of claim 1 wherein said flange means is defined by a first surface extending substantially radially inwardly from a interior surface of said rib means and a second surface extending at an incline from a point proximate an edge of said first surface to a point on said interior surface of said rib means proximate the edge thereof.

4. The device of claim 1 further comprising reinforced pull tab means extending substantially radially outwardly from said channel means.

5. The device of claim 4 wherein said pull tab means comprises substantially radially extending spaced rib means.

6. The device of claim 1 wherein said body is substantially solid and non-grooved.

7. An ostomy device comprising waste collection means, faceplate means attachable to a peristomal surface, means for detachably coupling said collection means on said faceplate means, said coupling means comprising first and second coupling rings affixed to said collection means and said faceplate means, respectively, said first coupling means comprising substantially radially extending pull tab means, said pull tab means comprising a base and substantially triangular radially extending means for reinforcing said base to increase the strength thereof, said substantially triangular radially extending means having a first side and a second side, said first side being located adjacent and extending axially along said ring of said first coupling means, and said second side extending radially outward along said base of said pull tab means.

8. The device of claim 7 wherein said reinforcing means comprises spaced, substantially parallel reinforcing rib means.

* * * * *